United States Patent [19]

Drabek

[11] Patent Number: 4,503,069
[45] Date of Patent: Mar. 5, 1985

[54] N-ALKYLIDENE-IMINO-OXYCARBONYL-N-METHYL-[2,2-DIMETHYL-2,3-DIHYDROBENZOFURANYL(7)]-CARBAMATES AND THEIR USE FOR CONTROLLING PESTS

[75] Inventor: Jozef Drabek, Oberwil, Switzerland

[73] Assignee: Ciba-Geigy Corporation, Ardsley, N.Y.

[21] Appl. No.: 492,110

[22] Filed: May 6, 1983

[30] Foreign Application Priority Data

May 17, 1982 [CH] Switzerland ............... 3053/82
Feb. 18, 1983 [CH] Switzerland ............... 902/83

[51] Int. Cl.³ .................... A01N 47/24; C07D 307/86
[52] U.S. Cl. ..................................... 514/469; 549/470
[58] Field of Search ................... 549/470; 424/285

[56] References Cited

U.S. PATENT DOCUMENTS 4,211,790 7/1980 Hartmann et al. ............... 549/470
4,410,543 10/1983 Drabek ............................ 549/470

Primary Examiner—Henry R. Jiles
Assistant Examiner—Bernard I. Dentz
Attorney, Agent, or Firm—Frederick H. Rabin

[57] ABSTRACT

N-Alkylidene-imino-oxycarbonyl-N-methyl-[2,2-dimethyl-2,3-dihydrobenzofuranyl(7)]-carbamates

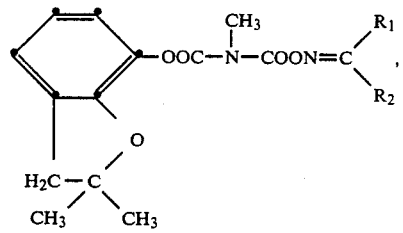

wherein $R_1$ and $R_2$ independently of one another are each an alkyl group, or together they are an alkylene group.

A process for producing these carbamates and their use for controlling pests are described.

9 Claims, No Drawings

N-ALKYLIDENE-IMINO-OXYCARBONYL-N-METHYL-[2,2-DIMETHYL-2,3-DIHYDROBENZOFURANYL(7)]-CARBAMATES AND THEIR USE FOR CONTROLLING PESTS

The present invention relates to N-alkylidene-iminooxycarbonyl-N-methyl-[2,2-dimethyl-2,3-dihydrobenzofuranyl(7)]-carbamates, to processes for producing them, and to their use for controlling pests.

The N-alkylidene-imino-oxycarbonyl-N-methyl-[2,2-dimethyl-2,3-dihydrobenzofuranyl(7)]-carbamates have the formula

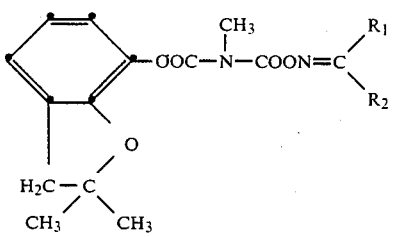

wherein $R_1$ and $R_2$ independently of one another are each an alkyl group, or together they are an alkylene group.

The alkyl groups $R_1$ and $R_2$ can be straight-chain or branched-chain, and have in the chain preferably 1 to 10 carbon atoms. Examples of such groups are, inter alia: methyl, ethyl, propyl, isoproyl, n-, i-, sec- or tert- butyl, n-pentyl, n-hexyl, n-heptyl, n-octyl, n-nonyl and n-decyl.

Alkylene groups $R_1$ and $R_2$ can be straight-chain or branched-chain, and have in the chain 2 to 9 carbon atoms. Examples of such groups are, inter alia: dimethylene, trimethylene, tetramethylene, pentamethylene, nonamethylene or

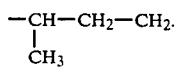

Preferred compounds of the formula I are those wherein $R_1$ and $R_2$ independently of one another are each a $C_1$-$C_{10}$-alkyl group, or together they are a $C_2$-$C_9$-alkylene group.

Compounds of the formula I which are particularly preferred are those wherein $R_1$ and $R_2$ independently of one another are each a $C_1$-$C_5$-alkyl group, or together they are a $C_3$-$C_9$-alkylene group. More especially preferred however are compounds of the formula I wherein $R_1$ is a $C_1$-$C_5$-alkyl group, $R_2$ is methyl, ethyl or propyl, or $R_1$ and $R_2$ together are the tetra- or pentamethylene group.

The compounds of the formula I can be produced by methods known per se, for example as follows:

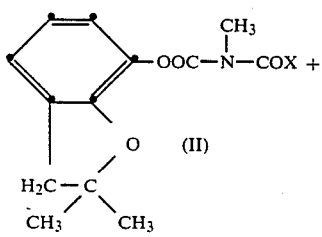

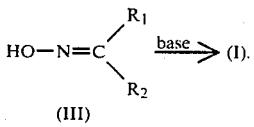

In the formulae II and III, the symbols $R_1$ and $R_2$ have the meanings defined under the formula I, and X is a halogen atom, particularly fluorine or chlorine.

The process is performed at a reaction temperature of between $-50°$ C. and $+130°$ C., preferably between $-10°$ C. and $+100°$ C., under normal or slightly elevated pressure and in the presence of a base, and optionally in the presence of a solvent or diluent which is inert to the reactants.

Suitable bases for this process are in particular: tertiary amines, such as trialkylamines, pyridines and dialkylanilines; also hydroxides, oxides, carbonates and bicarbonates of alkali metals and alkaline-earth metals, and also alkali metal alcoholates, for example potassium tert-butylate or sodium methylate.

Solvents or diluents which are suitable are for example: ethers and ethereal compounds, such as diethyl ether, di-isopropyl ether, dioxane or tetrahydrofuran; aliphatic and aromatic hydrocarbons, especially benzene, toluene and xylenes; and ketones, such as acetone, methyl ethyl ketone and cyclohexanone.

The starting materials of the formulae II and III are known, and can be produced by methods analogous to known methods.

The compounds of the formula I are suitable for controlling pests on animals and plants and in the soil.

The compounds of the formula I are suitable for controlling insects, for example of the orders; Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and for controlling mites and ticks of the order Acarina. The compounds of the formula I are above all suitable for controlling insects that damage plants, in particular insects that damage plants by eating, in crops of ornamental plants and productive plants, especially in cotton crops (for example against *Spodoptera littoralis* and *Heliothis virescens*), and in vegetable drops (for example against *Leptinotarsa decemlineata* and *Myzus persicae*), and for controlling soil insects (for example *Aulacophora femoralis, Chortophila brassicae, Pachnoda savignyi* and *Scotia ypsilon*). It is to be emphasised in this connection that the stated compounds are distinguished both by a strongly marked systemic action as well as contact action against sucking insects, and particularly against insects of the family Aphididae (for example *Aphis fabae, Aphis craccivora* and *Myzus persicae*), which are difficult to control by means hitherto known. Active substances of the formula I exhibit also a very favourable action against flies, such as *Musca domestica*, and against mosquito larvae. The compounds of the formula I are characterised also by a broad ovicidal and ovilarvicidal activity, and they have a valuable action against ectoparasitic mites and ticks, for example of the families: Ixodidae, Argasidae and Dermanyssidae.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or a grinding of the active ingredients with extenders, such as with solvents, solid carriers and optionally surface-active compounds (tensides).

Suitable solvents are: aromatic hydrocarbons, preferably the fractions $C_8$ $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms.

Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylene-diaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxythylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyl-trimethylammonium chloride or benzyldi(2-chloroethyl)ethylammonium bromide.

The tensides customarily used in formulation practice are described, inter alia, in the following publication:

"Mc Cutcheon's Detergents and Emulsifiers Annual", MC Publishing Corp., Ringwood, N.J., 1979.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25%, of a tenside. Whereas commercial products are preferably in the form of concentrated compositions, the compositions employed by the end-user are as a rule diluted.

The compositions can also contain additives such as stabilisers, antifoam agents, viscosity regulators, binders and adhesives, as well as fertilisers or other active ingredients for obtaining special effects.

| Formulation examples for liquid active ingredients of the formula I (% = percent by weight) | | | |
|---|---|---|---|
| 1. Emulsion concentrates | (a) | (b) | (c) |
| active ingredient | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 2. Solutions | (a) | (b) | (c) | (d) |
|---|---|---|---|---|
| active ingredient | 80% | 10% | 5% | 95% |
| ethylene glycol-monomethyl ether | 20% | — | — | — |
| polyethylene glycol MG 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

These solutions are suitable for application in the form of very small drops.

| 3. Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

| Formulation examples for solid active ingredients of the formula I (% = percent by weight) | | | |
|---|---|---|---|
| 5. Wettable powders | (a) | (b) | (c) |
| active ingredient | 25% | 50% | 75% |
| sodium lignin sulfonate | 5% | 5% | — |
| sodium laurylsulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 6. Emulsion concentrate | |
|---|---|
| active ingredient | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| active ingredient | 5% | 8% |
| talcum | 95% | — |
| kaolin | — | 92% |

Dusts ready for use are obtained by mixing the active ingredient with the carrier, and grinding the mixture in a suitable mill.

| 8. Extruder granulate | |
|---|---|
| active ingredient | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded and then dried in a stream of air.

| 9. Coated granulate | |
|---|---|
| active ingredient | 3% |
| polyethylene glycol (MG 200) | 3% |
| kaolin | 94% |

The finely ground active ingredient is evenly applied, in a mixer, to the kaolin moistened with polyethylene glycol. Dustfree coated granulates are obtained in this manner.

| 10. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32 |

The finely ground active ingredient is intimately mixed with the additives. There is obtained a suspension concentrate from which can be produced, by dilution with water, suspensions of the concentration required.

EXAMPLE 1

Production of the compound of the formula

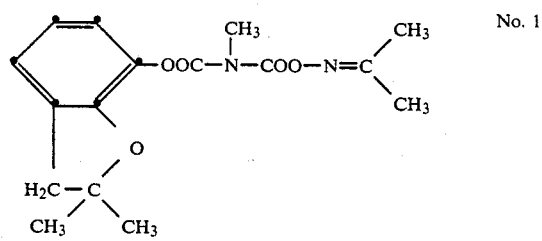

No. 1

4.83 g of triethylamine and 0.1 g of 4-dimethylaminopyridine are added dropwise at 0° to 10° C. within 30 minutes to a solution of 8.5 g of chlorocarbonyl-N-methyl[2,2-dimethyl-2,3-dihydrobenzofuranyl(7)] carbamate and 2.2 g of acetone oxime in 100 ml of toluene. After the reaction mixture has been stirred for 10 hours at 20° C., it is washed once with 100 ml of 0.05N hydrochloric acid solution and once with 100 ml of water. The reaction mixture is dried over sodium sulfate, and the toluene is then distilled off. The crude product is subsequently recrystallised from a mixture of hexane and toluene (1:1) to thus obtain the title compound having a melting point of 89° C.

The following compounds are produced in an analogous manner:

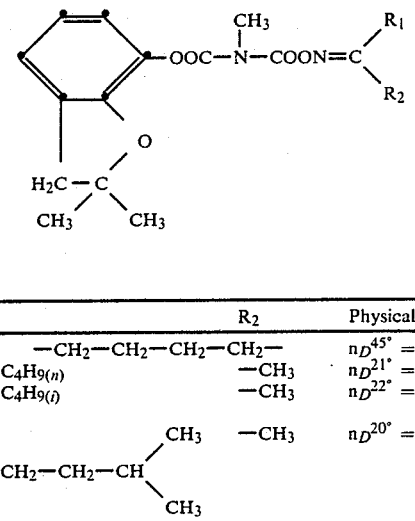

| No. | $R_1$ | $R_2$ | Physical data |
|---|---|---|---|
| 2 | —CH$_2$—CH$_2$—CH$_2$—CH$_2$— | | $n_D^{45°} = 1,5296$ |
| 3 | —C$_4$H$_{9(n)}$ | —CH$_3$ | $n_D^{21°} = 1,5189$ |
| 4 | —C$_4$H$_{9(i)}$ | —CH$_3$ | $n_D^{22°} = 1,5181$ |
| 5 | —CH$_2$—CH$_2$—CH(CH$_3$)CH$_3$ | —CH$_3$ | $n_D^{20°} = 1,5150$ |
| 6 | —C$_2$H$_5$ | —CH$_3$ | $n_D^{22°} = 1,5259$ |
| 7 | —C$_3$H$_{7(i)}$ | —CH$_3$ | $n_D^{20°} = 1,5202$ |
| 8 | —(CH$_2$)$_7$CH$_3$ | —C$_3$H$_{7(n)}$ | $n_D^{20°} = 1,5055$ |
| 9 | —(CH$_2$)$_9$CH$_3$ | —CH$_3$ | $n_D^{20°} = 1,5047$ |
| 10 | —CH$_2$—CH$_2$—CH$_2$— | | $n_D^{20} = 1,5312$ |
| 11 | —(CH$_2$)$_9$— | | $n_D^{40°} = 1,5250$ |
| 12 | —CH$_2$—CH$_2$—CH$_2$—CH$_2$—CH$_2$— | | m.p.: 95–100° C. |
| 13 | —C$_3$H$_{7(n)}$ | —C$_3$H$_{7(n)}$ | $n_D^{20°} = 1,5055$ |

EXAMPLE 2

Insecticidal systemic action: *Aphis craccivora*

Rooted bean plants are transplanted to pots each containing 600 ccm of soil; and 50 ml of a test solution containing 50 ppm, 12.5 ppm and 3 ppm, respectively, of the compound to be tested are subsequently poured directly onto the soil. After 24 hours, aphids (*Aphis craccivora*) are settled onto the parts of plants above the soil, and a plastics cylinder is placed over each plant and drawn to by tying at the bottom in order to protect the aphids from any contact or gas effects of the test substance. An evaluation of the mortality rate achieved is made 48 hours after commencement of the test. Two plants, each in a separate pot, are used per concentration level of test substance. The test is carried out at 25° C. with 70° relative humidity.

The compounds according to Example 1 exhibit against *Aphis craccivora* the degree of activity shown in the following Table.

Biological Test Results

In the following Table are summarized test results based on the Example given in the foregoing, the index of values with regard to the percentage mortality of the pests being as follows:

A: 70–100% mortality with 3 ppm of active ingredient,

B: 70–100% mortality with 12.5 ppm of active ingredient,

C: 70–100% mortality with 50 ppm of active ingredient.

| Compound No. | Activity against *Aphis craccivora* |
|---|---|
| 1 | A |
| 2 | B |
| 3 | B |
| 4 | A |
| 5 | A |
| 6 | A |
| 7 | B |
| 8 | A |
| 9 | B |
| 10 | B |
| 11 | B |
| 12 | A |
| 13 | B |

What is claimed is:

1. An N-alkylidene-imino-oxycarbonyl-N-methyl-[2,2-dimethyl-2,3-dihydrobenzofuranyl(7)]-carbonate of the formula

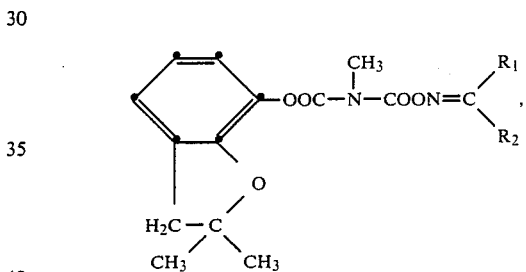

wherein $R_1$ and $R_2$ independently of one another are each a $C_1$–$C_{10}$ alkyl group, or together they are a $C_2$–$C_9$ alkylene group.

2. A compound according to claim 1, wherein $R_1$ and $R_2$ independently of one another are each a $C_1$–$C_5$-alkyl group, or together they are a $C_3$–$C_9$-alkylene group.

3. A compound according to claim 2, wherein $R_1$ is a $C_1$–$C_5$-alkyl group, $R_2$ is methyl, ethyl or propyl, or $R_1$ and $R_2$ together are the tetra- or pentamethylene group.

4. The compound according to claim 3 of the formula

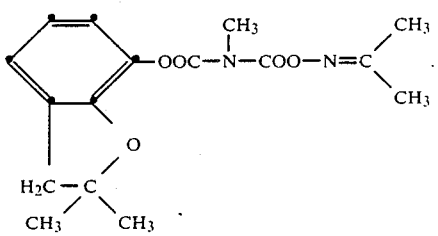

5. The compound according to claim 3 of the formula

6. The compound according to claim 3 of the formula

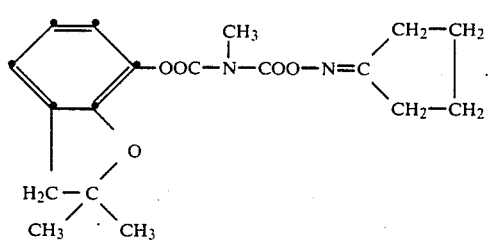

7. The compound according to claim 2 of the formula

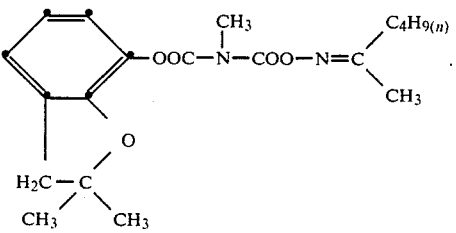

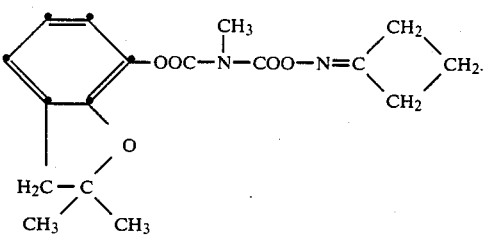

8. A method of controlling insects and acarids which comprises applying thereto or to the locus thereof an effective amount of a compound according to claim 1.

9. An insecticidal and acaricidal composition which comprises (1) an insecticidally or acaricidally effective amount of a compound according to claim 1 and (2) a carrier.

* * * * *